United States Patent [19]

Kalopissis et al.

[11] 4,288,622
[45] Sep. 8, 1981

[54] N,N-DIALKYLAMINO DIPHENYLAMINES AND THE USE THEREOF IN COMPOSITIONS FOR DYEING KERATINIC FIBERS

[75] Inventors: Grégoire Kalopissis, Neuilly-sur-Seine; Andrée Bugaut, Boulogne-sur-Seine; Françoise Estradier, Paris, all of France

[73] Assignee: L'Oreal, Paris, France

[21] Appl. No.: 741,495

[22] Filed: Nov. 12, 1976

Related U.S. Application Data

[62] Division of Ser. No. 551,653, Feb. 21, 1975, Pat. No. 4,008,999.

[30] Foreign Application Priority Data

Feb. 22, 1974 [LU] Luxembourg .............. 69459

[51] Int. Cl.$^3$ .............. C07C 91/42; D06P 1/32
[52] U.S. Cl. .............. 564/194; 8/410; 260/396 N; 564/50; 564/112; 564/434; 564/442; 564/443
[58] Field of Search .............. 260/571; 564/50, 194, 564/434

[56] References Cited

U.S. PATENT DOCUMENTS

| | | | |
|---|---|---|---|
| 1,806,040 | 5/1931 | Byers | 260/571 X |
| 2,101,879 | 12/1937 | Strouse | 260/571 |
| 2,692,262 | 10/1954 | Bosshard | 260/571 X |
| 3,271,452 | 9/1966 | Merz | 260/571 |
| 3,494,715 | 2/1970 | Streck | 8/8 |
| 3,787,174 | 1/1974 | Kalopissis et al. | 260/571 X |
| 3,792,090 | 2/1974 | Kalopissis et al. | 260/571 |
| 3,853,464 | 12/1974 | Kalopissis et al. | 260/571 X |

OTHER PUBLICATIONS

Allan et al., Chemical Abstracts, vol. 49, 207 to 208 (1954).
Bugai et al., Chemical Abstracts, vol. 55, 25462a (1961).
Fieser et al., J. Amer. Chem. Soc., vol. 61, pp. 376 to 383 (1939).
Fuortes et al., Chemical Abstracts, vol. 54, 9307 to 9308 (1960).
Jacobson, Chemical Abstracts, vol. 16, pp. 2318 to 2320 (1922).

*Primary Examiner*—Floyd D. Higel
*Attorney, Agent, or Firm*—Cushman, Darby & Cushman

[57] ABSTRACT

Diphenylamine of the formula

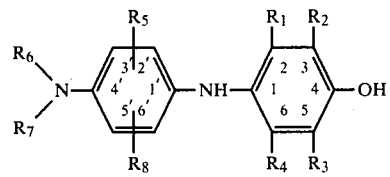

wherein
  $R_1$ and $R_4$ each independently represent a member selected from the group consisting of hydrogen, halogen, lower alkyl having 1–6 carbon atoms, lower alkoxy having 1–6 carbon atoms, amino, lower alkyl amino wherein the alkyl moiety has 1–6 carbon atoms, acylamino, lower carbamylalkyl amino wherein the alkyl moiety has 1–6 carbon atoms, lower hydroxyalkyl amino wherein the alkyl moiety has 1–6 carbon atoms, lower carbalkoxy amino wherein the alkoxy moiety has 1–6 carbon atoms and ureido;
  $R_2$ and $R_3$ each independently represent a member selected from the group consisting of hydrogen, halogen, lower alkyl having 1–6 carbon atoms, lower alkoxy having 1–6 carbon atoms, acylamino and ureido;
  $R_5$ and $R_8$ each independently represent a member selected from the group consisting of hydrogen, halogen, lower alkyl having 1–6 carbon atoms and lower alkoxy having 1–6 carbon atoms; and
  $R_6$ and $R_7$ are lower alkyl having 1–6 carbon atoms, with the proviso that (a) when both $R_6$ and $R_7$ represent methyl (1) one of $R_1$ and $R_4$ must represent a member selected from the group consisting of amino, lower alkyl amino wherein the alkyl moiety has 1–6 carbon atoms, lower carbamylalkyl amino wherein the alkyl moiety has 1–6 carbon atoms, lower hydroxyalkyl amino wherein the alkyl moiety has 1–6 carbon atoms and ureido, or (2) one of $R_1$ and $R_4$ represent acylamino and $R_2$ and $R_3$ are not both hydrogen, and (b) that when both $R_6$ and $R_7$ represent ethyl, $R_2$ and $R_3$ are other than tertiobutyl.

The said diphenylamine is employed in a dye composition for dyeing keratinic fibers.

4 Claims, No Drawings

N,N-DIALKYLAMINO DIPHENYLAMINES AND THE USE THEREOF IN COMPOSITIONS FOR DYEING KERATINIC FIBERS

This is a division of application Ser. No. 551,653 filed Feb. 21, 1975 U.S. Pat. No. 4,008,999.

The present invention relates to diphenylamines or N-alkyl leuco indoanilines disubstituted in the 4' position, to their preparation and to their use for dyeing keratinic fibers, and in particular living human hair.

A currently utilized technique for dyeing keratinic fibers, and especially living human hair, comprises applying to the hair, in the presence of an oxidizing agent added at the moment of use (generally hydrogen peroxide), a dye composition comprising a mixture in an appropriate cosmetic support, of compounds belonging to one or the other of the two following classes.

The first class of compounds, generally called "oxidation bases" is principally constituted by paraphenylenediamines or paraaminophenols which, on oxidation, produce para benzoquinonediimines or parabenzoquinonemonoimines.

The second class of compounds, generally called "couplers" include, especially, metaaminophenols, metaacetylaminophenols, metadiamines and metadiphenols. They are compounds, with which when the benzoquinone mono- or di-imines, will react to produce dyes called, depending upon their structure, indophenols, indoanilines or indamines.

These dyes, which provide a range of shades of exceptional richness, are primarily characterized by the luminosity and the richness in glints of dyeings or colorations they impart to the fibers dyed therewith.

However, when a complex dye composition is employed, i.e. a composition which includes several bases and several couplers, it is very difficult to foresee in the final shade the contribution of each possible couple of oxidation base and coupler. In other words, on the one hand, it is very difficult at the outset to predict with any exactitude the final shade that will be attained and, on the other hand, for a given dye composition, it is not often easy to be assured of a perfectly reproducible result. These difficulties are increased by the fact that different secondary reactions can modify the final shade, such secondary reactions including, for instance, formation of Bandrowsky base type compounds from the with oxidation bases; recondensation of a molecule of an oxidation base on certain indophenols or on certain indoanilines or indamines; and formation of quinones and the like.

Heretofore, it has also been proposed to use in the dyeing of hair, some indoanilines which are well defined compounds and which impart to the hair essentially perfectly reproducible shades.

However, some inconvenience has been experienced in the use of these compounds since they possess only a slight affinity for keratinic fibers under conventional conditions for dyeing hair.

The present invention relates to leuco derivatives of indoanilines which are colorless compounds and which, when applied in an aqueous solution to fibers to be dyed, are oxidized at the interior of the keratinic fibers so as to give the corresponding indoanilines. These resulting indoanilines are the colored compounds which are directly responsible for the dyeing of the fibers. The colorations thus obtained exhibit fastness and intensity of coloration which are greater than those of dyeings effected by the direct application of indoanilines, because of the enhanced solubility and better keratinic fiber penetration characteristics of the compounds of the present invention.

The oxidation of leuco derivatives of the present invention to indoanilines can be effected by the oxygen in air or by the use of an oxidizing agent incorporated into the dye composition at the moment of use. Representative oxidizing agents include hydrogen peroxide, urea peroxide and ammonium persulfate.

While the use of the leuco derivatives of indoanilines for dyeing hair has already been proposed, the present invention enlarges the family of such leuco derivatives. Thus the leuco derivatives of indoanilines or diphenylamines of the present invention have the formula

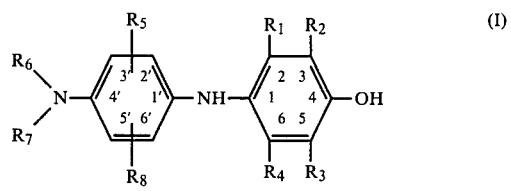

wherein
$R_1$ and $R_4$ each independently represent a member selected from the group consisting of hydrogen, halogen, lower alkyl, lower alkoxy, amino, lower alkyl amino, acylamino, lower carbamylalkyl amino, lower hydroxyalkyl amino, lower carbalkoxy amino and ureido;

$R_2$ and $R_3$ each independently represent a member selected from the group consisting of hydrogen, halogen, lower alkyl, lower alkoxy, acylamino and ureido;

$R_5$ and $R_8$ each independently represent a member selected from the group consisting of halogen, lower alkyl and lower alkoxy; and $R_6$ and $R_7$ represent lower alkyl with the proviso that (a) when both $R_6$ and $R_7$ represent methyl, (1) one of $R_1$ and $R_4$ must represent a member selected from the group consisting of amino, lower alkyl amino, lower carbamylalkyl amino, lower hydroxyalkyl amino and ureido, or (2) one of $R_1$ and $R_4$ represent acylamino and $R_2$ and $R_3$ are not both hydrogen; and (b) that when both $R_6$ and $R_7$ represent ethyl, $R_2$ and $R_3$ are other than tertiobutyl.

The terms lower alkyl and lower alkoxy mean alkyl and alkoxy containing 1-6 carbon atoms, preferably 1-4 carbon atoms.

The presence of alkyl substituents as $R_6$ and $R_7$ results in shifting the colors obtained towards the blues.

The present invention also relates to diphenylamines of formula (I) in the form of their salts such as, for instance, the hydrochlorides, hydrobromides, sulfates and phosphates thereof.

The diphenylamines of formula (I) are the leuco derivatives of indoanilines of formula (II)

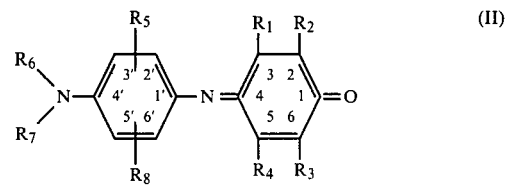

wherein $R_1$, $R_2$, $R_3$, $R_4$, $R_5$, $R_6$, $R_7$ and $R_8$ have the meanings given above.

The indoanilines of formula (II) can be prepared by the condensation of a substituted aniline of formula (III)

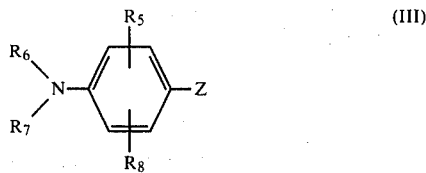

(III)

wherein Z represents NO or $NH_2$ and $R_5$, $R_6$, $R_7$ and $R_8$ have the meanings given above, or a salt thereof, on a phenolic compound of the formula (IV)

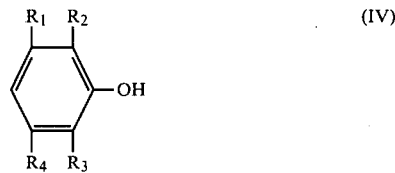

(IV)

wherein $R_1$, $R_2$, $R_3$ and $R_4$ have the meanings given above, or a salt thereof.

When Z represents $-NH_2$, the condensation is carried out in an aqueous, hydroalcoholic or hydroacetonic medium, at an alkaline pH generally greater than 8, in the presence of an oxidizing agent such as, for example, ammonium persulfate, potassium ferricyanide and hydrogen peroxide and at a temperature ranging generally between about 0° to 25° C. The alkaline pH is obtained by the addition to the reaction medium of ammonia or an alkaline carbonate such as sodium carbonate.

The molar ratio of substituted phenol to substituted aniline can range between about 1:0.5 to 1:1.2 and is, preferably about 1:1. The molar ratio of oxidizing agent to substituted phenol ranges from about 1:1 to 4:1 and is preferably between about 1:1 and 2:1 when ammonium persulfate is employed as the oxidizing agent. This molar ratio is about 8:1 when hydrogen peroxide is employed as the oxidizing agent. Hydrogen peroxide is usually used in the form of a 6 weight percent solution thereof. The reaction medium can be water, a lower alkanol which preferably is ethanol, propanol or isopropanol, an acetone-water mixture or a lower alkanol-water mixture wherein said mixtures the ratio of acetone or alkanol to water ranges between about b 1:3 to 2:1.

When Z represents —NO the condensation is generally carried out at a temperature ranging between about 30° to 60° C., preferably 40° to 55° C., in an ethanol-water mixture, preferably a 1:1 mixture thereof, which is either neutral or has been made alkaline by the addition thereto of a dilute solution of sodium hydroxide. The condensation is carried out in the absence of an oxidizing agent.

The reduction of the indoanilines (benzoquinoneimines) of Formula II is carried out using an alkaline hydrosulfite, preferably sodium hydrosulfite, in the presence of sodium hydroxide or acetic acid. Alternatively the reduction can be effected using an alkaline sulfide, preferably ammonium sulfide or by catalytic hydrogenation in the presence of a palladium on charcoal catalyst.

According to a first advantageous method of reducing the indoanilines, excess sodium hydrosulfite is dissolved in an aqueous solution of 1 N NaOH. To the resulting solution there is added, over a period of about 15 to 30 minutes, while stirring the mixture and maintaining the temperature thereof between about 0° to 30° C., the benzoquinoneimine in solution or suspension in ethanol.

Agitation of the resulting mixture is continued until the solution becomes colorless which generally requires between about 15-60 minutes. The desired diphenylamine (leuco indoaniline) is precipitated by cooling the reaction mixture to 0° C. For certain diphenylamines it is, moreover, necessary to acidify the solution, for example by the addition thereto of acetic acid (see Examples 4, 5, 9, 10, 11, 13 and 14 infra) or of carbonic gas (see Example 12 infra). Cooling to 0° C. is effected with the use of ice or solid carbon dioxide, the latter serving both to cool the reaction mixture and to acidify the same (see Examples 7, 8 and 15 infra).

According to a second method of reducing the benzoquinoneimines, the benzoquinoneimine is dissolved in ethanol (95° titer). To the resulting solution there is added, at ambient temperature, a solution of ammonia saturated with hydrogen sulfide. The desired diphenylamine is precipitated by the addition thereto of water (see Example 6, infra).

The diphenylamine of Example 3, below, has been prepared in accordance with a third method according to which excess sodium hydrosulfite is dissolved in a 10% aqueous solution of acetic acid. To this solution, maintained at a temperature between about 15°-20° C., there is added, while stirring the same, the benzoquinoneimine in the form of an ethanol solution thereof. Stirring is continued until the solution becomes colorless which is effected in proportion to the addition of the benzoquinoneimine. The solution is then neutralized with ammonia to the point of the precipitation of the diphenylamine in crystalline form which precipitation occurs at a pH of about 5 to 7.5.

According to a fourth method of reducing the benzoquinoneimines, as seen for instance in Examples 1 and 2 below, 0.004 mole of benzoquinoneimine is partially dissolved in 150 ml of absolute ethanol. There is then added thereto 0.2 g of palladium on charcoal (10 weight percent palladium) as a catalyst and the indoaniline is reduced by hydrogenation under atmospheric pressure. The reaction mixture is then filtered to recover the catalyst after which the remaining mixture is concentrated under a vacuum and under a nitrogen atmosphere. The desired diphenylamine is then precipitated in the form of crystals by the addition of ice water or in the form of a salt by the addition of an acid.

The diphenylamines of the present invention are usefully employed for dyeing keratinic fibers and, in particular, living human hair.

These diphenylamines, when applied to hair in an aqueous or hydroalcoholic solution, at a concentration ranging between about 0.002 to 5 weight percent thereof, and preferably between 0.02 to 3 weight percent, provide, after oxidation, either with air or by another oxidizing agent such as hydrogen peroxide, urea peroxide or ammonium persulfate, a range of shades which are very rich in the area of pinks to violets, blues and greens. Additionally, the diphenylamines of the present invention provide some very luminous grays and beiges which are rich in glints.

The present invention also relates to a composition for dyeing keratinic fibers, particularly living human hair, comprising an aqueous solution or hydroalcoholic solution, preferably hydroethanolic or hydroisopropanolic, of at least one diphenylamine of Formula (I) wherein $R_1$ and $R_4$ each independently represent a member selected from the group consisting of hydrogen, halogen, lower alkyl, lower alkoxy, amino, lower alkyl amino, acylamino, lower carbamylalkyl amino, lower hydroxyalkyl amino, lower carbalkoxy amino and ureido; $R_2$ and $R_3$ each independently represent a member selected from the group consisting of hydrogen, halogen, lower alkyl, lower alkoxy, acylamino and ureido; $R_5$ and $R_8$ each independently represent a member selected from the group consisting of hydrogen, halogen, lower alkyl and lower alkoxy; and $R_6$ and $R_7$ represent lower alkyl. As indicated above, said lower alkyl and lower alkoxy groups or moieties contain 1–6 and preferably 1–4 carbon atoms.

The dye composition of the present invention can also include a salt of the diphenylamines of Formula (I) and in particular the hydrochloride, hydrobromide, sulfate or phosphate thereof.

The dye compositions according to the present invention can include as the active dyeing agent only the compounds of formula (I). However, they can also include other known leuco derivatives of indoanilines, indamines or indophenols, or even oxidation dyes such as ortho- or para-phenylenediamines or ortho- or para-aminophenols, as well as benzene compounds trisubstituted or tetrasubstituted by hydroxy, amino or alkoxy groups and couplers such as metadiamines, metadiphenols, metaaminophenols, metaacetylaminophenols or even direct dyes such as nitrobenzene dyes, azo dyes or anthraquinone dyes, indoanilines, indamines and/or indophenols.

The compositions according to the present invention are generally provided in the form of an aqueous or hydroalcoholic solution containing one or more compounds of formula (I), in admixture or not with other dyes. They can, however, also include thickening agents and be provided in the form of a cream or gel.

Representative thickening agents that can be incorporated into the dye composition of the present invention include cellulose derivatives such as methyl cellulose, hydroxyethyl cellulose, carboxymethyl cellulose or acrylic polymers such as the sodium salt of polyacrylic acid or carboxyvinyl polymers.

The dye composition can contain as solvents, water, lower alkanols for example ethanol or isopropanol, polyalcohols such as glycols, for example, ethylene glycol, propylene glycol, butyl glycol, diethyleneglycol and the monomethyl ether of diethylene glycol.

The dye composition according to the present invention can also include other components generally employed in cosmetics, such as surface active agents used as carriers, as thickening agents, as dispersants or as wetting agents; swelling agents; penetrating agents; emollients; polymers and/or perfumes. The composition of the present invention can also be packaged in aerosol containers together with an aerosol propellant.

Representative surface active agents include oxyethylenated alcohols and particularly oxyethylenated lauryl alcohol, partially sulfated oxyethylenated lauryl alcohol and preferably a mixture of 19% partially sulfated lauryl alcohol oxyethylenated with 2 moles of ethylene oxide and 81% of the sodium sulfate salt of this same oxyethylenated alcohol, the alkaline salts or ammonium sulfates of long chain fatty alcohols, for example, ammonium lauryl sulfate, oxyethylenated alkylphenols and preferably nonylphenol oxyethylenated with 4 or 9 moles of ethylene oxide per mole of alkylphenol, oxyethylenated fatty acids and the sulfates and sulfonates of fatty alcohols optionally oxyethylenated.

Representative aerosol propellants usefully employed in compositions according to the present invention include nitrogen, nitrous oxide, volatile hydrocarbons such as butane, isobutane or propane, or preferably fluorinated hydrocarbons (sold under the name of Freon by Dupont) such as as dichlorodifluoromethane, 1,1-difluoromethane, 1,2-dichloro-1,1,2,2-tetrafluoro ethane and 1-chloro-1,1-difluoromethane. Mixtures of two or more hydrocarbons or fluorinated hydrocarbons can also be used.

The pH of the compositions of the present invention can vary widely and generally it ranges between about 4.5 to 12 and preferably between about 6.5 and 10.5.

The pH of the composition can be adjusted with the aid of an alkalizing agent such as, for example, ammonia, mono-, di- or tir-ethanolamine, di- or tri-sodium phosphate, sodium carbonate or potassium carbonate, or with the aid of an acidifying agent such as, for example, acetic acid, lactic acid, phosphoric acid or citric acid.

The dyeing of keratinic fibers and, in particular, living human hair, with the use of the dye compositions of the present invention, is carried out in a conventional manner by applying the said composition to the fibers to be dyed, permitting said composition to remain to contact with the fibers for a period of time ranging from about 5 to 30 minutes, rinsing and optionally washing the fibers and then drying the fibers. Prior to applying the said composition to the fibers, there can be added to said composition an oxidizing agent such as 30 to 100 percent by volume of hydrogen peroxide, generally 6% (20 volumes), or 0.1 to 15% by weight of an oxidizing agent such as urea peroxide or ammonium persulfate.

The compositions according to the present invention, when present in the form of a hydroalcoholic solution, can also include a cosmetic resin, so as to provide a colored hair setting lotion, which can be applied to wet or moist hair before setting.

Representative cosmetic resins that can be used in the hair setting lotion composition of the present invention include such film-forming polymers as polyvinylpyrrolidone; copolymers of polyvinylpyrrolidone and vinyl acetate; copolymers of vinyl acetate and an unsaturated carboxylic acid such as crotonic acid; copolymers resulting from the copolymerization of vinyle acetate, crotonic acid and an acrylic or methacrylic ester; copolymers resulting from the copolymerization of vinyl acetate and a vinyl alkyl ether; copolymers resulting from the copolymerization of vinyl acetate, crotonic acid and a vinyl ester of a long carbon chain acid or even of an allyl or methallyl ester of a long carbon chain acid; copolymers resulting from the copolymerization of an ester derived from an unsaturated alcohol and a short carbon chain acid, of an unsaturated short carbon chain acid and of at least one ester derived from a short carbon chain saturated alcohol and an unsaturated acid; and copolymers resulting from the copoymerization of at least one unsaturated ester and at least one unsaturated acid.

Representative preferred cosmetic resins include polyvinylpyrrolidone having a molecular weight ranging between about 10,000 to 360,000; copolymers of 10% crotonic acid and 90% vinyl acetate having a molecular weight ranging between about 10,000 or 70,000; copolymers of vinylpyrrolidone and vinyl actate having a molecular weight ranging between about 30,000 to 200,000 wherein the ratio of VP to VA ranges between 30:70 to 70:30; copolymers of maleic anhydride and methyl vinyl ether in a 1 to 1 molar ratio, having a specific viscosity, measured at 25° C. and at a concentration of 1 g in 100 ml of methylethylketone ranging between about 0.1 and 3.5; the monoethyl, monoisopropyl and monobutyl esters of said maleic anhydride-methyl vinyl ether copolymers; copolymers of maleic anhydride and vinylbutyl ether in a 1 to 1 molar ratio; terpolymers of methyl methacrylate (15–25%) stearyl methacrylate (25–35%) and dimethylaminoethyl methacrylate (52–62%), preferably quaternized for example by dimethyl sulfate, and the viscosity of which, measured at the boiling point of the ether and at a concentration of 5% in dimethylformamide, ranges between about 8–12 centipoises and terpolymers of vinyl acetate (75–85%), allyl stearate (10–20%) and allyloxy acetic acid (3–10%), the viscosity of which, measured at the boiling point of ether and at a concentration of 5% in dimethylformamide ranges between about 4.4 and 5 centipoises.

These cosmetic film-forming resins are used generally in an amount between about 1–3 percent by weight of the total hair setting lotion composition.

The alcohols generally employed in the production of the hair setting lotion compositions of the present invention are low molecular weight alcohols, preferably ethanol or isopropanol. These alcohols are used in an amount of about 20 to 70 weight percent of the total composition.

The hair setting lotion composition of the present invention can be utilized in a conventional manner by applying the same to wet or moist hair, previously washed and rinsed, followed by rolling the hair up on curlers and drying the hair.

The present invention is illustrated by the following non-limiting examples. These examples are tabulated in Tables I, I-bis, II, III and IV.

Examples of preparing the diphenylamines of the present invention appear in Tables I, I-bis and II. Table I, which indicates the characteristics of the prepared diphenylamines, has 9 columns numbered (1) through (9). Column (1) indicates the number of the example of preparation; the name of the compound prepared appears in column (2); columns (3) and (4) indicate, respectively, the melting point and the empirical formula; columns numbered (5) through (9) indicate, respectively, the percentages of C, H, N, Cl and S. For each compound prepared, columns (5) through (9) carry two to three lines, the first line indicating the theoretical percentages corresponding to the empirical formula of column (4), while the second and third lines indicate the percentages found by analysis.

Table I-bis indicates the characteristics of the benzoquinoneimines (indoanilines) which serve as an initial reactant in the preparation of the dipenylamines appearing in Table I. Table I-bis carries the same columns as Table I.

Table II, which indicates the manner in which the benzoquinoneimines appearing in Table I-bis are prepared, includes eight columns. Column (1) indicates, as in Table I, the number of the example of preparation. The columns following are numbered (II) through (17). Columns (11) and (12) indicate the name of the initial reactants, i.e. the substituted aniline in column (11) and substituted phenol in column (12). Column 13 entitled "ratio of (12):(11)" indicates the molar ratio between the substituted phenol and substituted aniline initial reactants.

Column (14) indicates the reaction medium; column (15), the nature of the oxidizing agent used; column (16) entitled "ratio of (15):(12)" indicates the molar ratio between the oxidizing agent and the substituted phenol; and column (17) indicates the reaction temperature in centigrade degrees.

The examples of use include examples of simple dye compositions as well as dye compositions which also include a cosmetic resin and are called hair setting lotions. All examples of use are tabulated in Table III.

Table III carries 13 columns numbered (31) to (43). Column (31) indicates the number of the example of use. This column carries a number preceded by the letter A. column (32) carries a figure which corresponds to a number appearing in column (1) of table I and indicates the diphenylamine used, or carries the letter C followed by a number which represents another dye used in admixture with the diphenylamine. The name of this dye appears at the bottom of the Table. Column (33) indicates the quantity of dye, expressed in percent by weight of the total weight of the composition. Columns (34) and (35) indicate, respectively, the nature and the weight percent of adjuvants used, based on the total weight of the sample dye composition or the hair setting lotion composition. In these columns appear the surface active agent, the thickening agent, the cosmetic polymer and all other components used in the dye composition and hair setting lotion composition.

Columns (36) and (37) indicate, respectively, the nature and the percent by weight of the total weight of the composition, of the solvent used other than water. The percent by weight of water used represents the difference between 100 g and the total weight appearing in columns (33), (35) and (37).

Columns (38), (39) and (40) indicate, respectively, the nature, the volume (expressed in ml) and the concentration of the solution of the oxidizing agent added to 100 g of the composition.

Column (41) indicates the pH of the composition while column (43) indicates the color obtained on bleached hair (D) or on 95% naturally white hair (B 95), this latter indication appearing in column (42).

In columns (32), (34), (36) and (38), there appear the names, respectively, of dyes other than the diphenylamines of the present invention, the adjuvants which include the polymers, the solvents and the oxidizing agents. These indications are given by abbreviations, for which the meanings, and in the case of the polymers, such characteristics as molecular weight or viscosity, appear at the bottom of the Tables. Unless indicated to the contrary, all percentages are by weight of the total weight of the dye composition or the hair setting lotion composition.

TABLE I

| Ex. No. (1) | DIPHENYLAMINES (2) | M.P. (C.°) (3) | EMPIRICAL FORMULA (4) | ANALYSIS | | | | |
|---|---|---|---|---|---|---|---|---|
| | | | | C % (5) | H % (6) | N % (7) | Cl % (8) | S % (9) |
| 1 | 3-methyl-4-hydroxy-6-amino-4'-dimethylamino diphenylamine | 170 | $C_{15}H_{19}N_3O$ M.W. = 257[a] M.W. = 263[b] | 70.03 69.75 69.82 | 7.39 7.58 7.50 | 16.34 16.44 16.38 | | |
| 2 | 3,5-dimethyl-2-amino-4-hydroxy-4'-dimethylamino diphenylamine trihydrochloride | 220 | $C_{16}H_{24}ON_3Cl_3$ | 50.46 50.31 50.29 | 6.37 6.24 6.32 | 11.04 10.97 11.03 | 27.94 27.74 27.69 | |
| 3 | 4-hydroxy-3-methyl-6-ureido-4'-N,N-dimethyl-amino diphenylamine | 260 | $C_{16}H_{20}N_4O_2$ | 63.98 63.60 63.63 | 6.71 6.84 6.82 | 18.65 18.58 18.45 | | |
| 4 | 3,5-dimethyl-4-hydroxy-2-acetylamino-4'-N,N-dimethylamino diphenylamine | 204 | $C_{18}H_{23}N_3O_2$ | 69.01 68.73 68.81 | 7.35 7.47 7.35 | 13.41 13.34 13.35 | | |
| 5 | 3-methyl-4-hydroxy-6-carbamylmethylamino-4'-N,N-dibutylamino diphenylamine | 148 | $C_{23}H_{34}N_4O$ | 69.31 69.30 69.76 | 8.60 8.53 8.43 | 14.06 14.12 14.17 | | |
| 6 | 2-chloro-4-hydroxy-5-ureido-2'-methyl-4'-N,N diethylamino diphenylamine | 194 | $C_{18}H_{23}N_4O_2Cl$ | 59.58 59.33 59.05 | 6.34 6.47 6.59 | 15.42 15.44 15.43 | 9.79 9.61 9.69 | |
| 7 | 3,5-dimethyl-2-amino-4-hydroxy-4'-N,N-diethyl-amino-2'-chloro diphenylamine | 92 | $C_{18}H_{24}N_3OCl$ | 64.77 64.50 | 7.28 7.17 | 12.59 12.65 | 10.64 10.54 | |
| 8 | 3,6-dimethyl-4-hydroxy-4'-N,N-dimethylamino diphenylamine | 140 | $C_{16}H_{20}N_2O$ | 74.96 74.72 | 7.86 7.71 | 10.93 10.86 | | |
| 9 | 3,5-dimethyl-4-hydroxy-2-amino-4-40 -N,N-dimethyl-amino-2'-methoxy diphenylamine | 153 | $C_{17}H_{23}N_2O_2$ | 67.75 67.71 | 7.69 7.54 | 13.94 14.04 | | |
| 10 | 3-methoxy-4-hydroxy-6-acetylamino-4'-N,N-di-methylamino diphenylamine | 202 | $C_{17}H_{21}N_3O_3$ | 64.76 64.84 | 6.67 6.50 | 13.33 13.57 | | |
| 11 | 3,3'-dichloro-4-hydroxy-6-acetylamino-4'-N,N-dimethylamino diphenylamine | 236 | $C_{16}H_{17}N_3O_2Cl_2$ | 54.24 53.96 | 4.85 4.90 | 11.86 11.91 | | |
| 12 | 3,5,2',6'-tetramethyl-4-hydroxy-2-ureido-4'-N N-dimethylamino diphenylamine | >260 with decomposition | $C_{19}H_{26}N_4O_2$ | 66.64 66.45 | 7.65 7.48 | 16.36 16.12 | | |
| 13 | 3-methyl-4-hydroxy-6-carbamylmethylamino-4'-N,N-dimethylamino-3'-methyl diphenylamine | 218 | $C_{18}H_{24}N_4O_2$ | 65.53 66.10 | 7.37 7.54 | 17.06 16.86 | | |
| 14 | 3-methyl-4-hydroxy-6-β-hydroxyethylamino-2' chloro-4'-N,N-dimethylamino diphenylamine | 135 | $C_{17}H_{22}N_3O_2Cl$ | 60.80 60.53 | 6.56 6.47 | 12.52 12.77 | | |
| 15 | 3-methyl-4-hydroxy-6-carbethoxyamino-4'-N,N-di-methylamino-3'-chloro diphenylamine | 172 | $C_{18}H_{22}N_3O_3Cl$ | 59.42 59.14 | 6.05 6.09 | 11.55 11.72 | | |
| 16 | 3-methyl-4-hydroxy-6-acetylamino-3'-chloro-4'-N,N-dimethylamino diphenylamine | 208 | $C_{17}H_{20}N_3O_2Cl$ | 61.17 61.07 | 6.00 6.08 | 12.59 12.44 | 10.64 10.63 | |
| 17 | 3,5-dimethyl-4-hydroxy-2-acetylamino-3'-chloro-4'-N,N-diemthylamino diphenylamine | 205 | $C_{18}H_{22}N_3O_2Cl$ | 62.16 62.13 | 6.35 6.41 | 12.09 12.20 | | |
| 18 | 3,5,2',6'-tetramethyl-4-hydroxy-2-acetylamino-4'-N,N-dimethylamino diphenylamine | 260 | $C_{20}H_{27}N_3O_2$ | 70.35 69.42 | 7.97 7.96 | 12.31 11.99 | | |
| 19 | 3,2',6'-trimethyl-4-hydroxy-6-amino-4'-N,N-di-methylamino diphenylamine | 189 | $C_{17}H_{23}N_3O$ | 71.54 71.80 | 8.12 8.33 | 14.73 14.79 | | |
| 20 | 3,2'-dimethyl-4-hydroxy-6-carbamylmethyl-amino 4'-N,N-dimethylamino diphenylamine | 201 | $C_{18}H_{24}N_4O_2$ | 65.83 65.91 | 7.37 7.35 | 17.06 17.29 | | |
| 21 | 3,5-dimethyl-4-hydroxy-3'-chloro-4'-N,N-dimethyl-amino diphenylamine | 97 | $C_{16}H_{19}N_2OCl$ | 66.09 66.05 | 6.54 6.46 | 9.63 9.60 | | |
| 22 | 3,5,2',6'-tetramethyl-4-hydroxy-4'-N,N-dimethyl-amino diphenylamine | 140 | $C_{18}H_{24}N_2O$ | 76.02 75.98 | 8.51 8.64 | 9.85 9.66 | | |

[a] molecular weight calculated
[b] molecular weight found by potentiometric titration in acetic acid with a 0.1 N solution of perchloric acid

TABLE I bis

| Ex. No (1) | BENZOQUINONEIMINES (2) | M.P. (C.°) (3) | EMPIRICAL FORMULA (4) | ANALYSIS | | | | |
|---|---|---|---|---|---|---|---|---|
| | | | | C % (5) | H % (6) | N % (7) | Cl % (8) | S % (9) |
| 1 | N-[(4'-(dimethylamino)phenyl] 6-methyl-3-amino benzoquinoneimine | 255 | $C_{15}H_{17}N_3O$ | 70.58 70.45 | 6.66 6.82 | 16.47 16.34 | | |
| 2 | N-[4'-(dimethylamino)phenyl] 2,6-dimethyl-3-amino benzoquinoneimine | 178 | $C_{16}H_{19}N_3O$ | 71.34 71.41 71.57 | 7.11 7.19 7.26 | 15.60 15.45 15.57 | | |
| 3 | N-[4'-(dimethylamino)phenyl] 2-methyl-5-ureido benzoquinoneimine | 275 | $C_{16}H_{18}N_4O_2$ | 64.41 64.29 64.44 | 6.37 6.21 6.26 | 18.78 19.01 18.93 | | |
| 4 | N-[4'-dimethylamino)phenyl] 2,6-dimethyl-3-acetylamino benzoquinoneimine | 111 | $C_{18}H_{21}N_3O_2$ | 69.43 69.13 69.25 | 6.80 6.64 6.74 | 13.50 13.72 13.60 | | |
| 5 | N-[4'-(dibutylamino)phenyl] 2-methyl-5-carba-mylmethylamino benzoquinoneimine | 169 | $C_{23}H_{32}N_4O_2$ | 69.66 69.80 69.68 | 8.13 8.23 8.26 | 14.13 14.04 13.98 | | |

TABLE I-continued

| Ex. No (1) | BENZOQUINONEIMINES (2) | bis M.P. (C.°) (3) | EMPIRICAL FORMULA (4) | ANALYSIS C % (5) | H % (6) | N % (7) | Cl % (8) | S % (9) |
|---|---|---|---|---|---|---|---|---|
| 6 | N-[(4'-diethylamino-2'methyl)phenyl] 3-chloro-6-ureido benzoquinoneimine | 225 | $C_{18}H_{21}N_4O_2Cl$ | 59.91 59.27 59.36 | 5.83 5.72 5.66 | 15.53 15.36 15.41 | 9.84 9.75 10.00 | |
| 7 | N-[4'-diethylamino-2'-chloro)phenyl] 2,6-dimethyl-3-amino benzoquinoneimine | 160 | $C_{18}H_{22}N_3OCl$ | 65.15 65.04 65.14 | 6.65 6.72 6.74 | 12.67 12.73 12.69 | 10.70 10.84 10.92 | |
| 8 | N-[(4'-dimethylamino)phenyl] 2,5-dimethyl benzoquinoneimine | 127 | $C_{16}H_{18}N_2O$ M.W. = 254$^{(a)}$ M.W. = 254$^{(b)}$ | | | | | |
| 9 | N-[(4'-dimethylamino-2'methoxy)phenyl] 2,6-dimethyl-3-amino benzoquinoneimine | 152 | $C_{17}H_{21}N_3O_2$ | 68.20 68.09 | 7.07 7.21 | 14.04 14.23 | | |
| 10 | N-[4'-(dimethylamino)phenyl] 2-methoxy-5-acetylamine benzoquinoneimine | 251 | $C_{17}H_{19}N_3O_3$ | 65.18 64.97 | 6.07 6.20 | 13.42 13.22 | | |
| 11 | N-[(4'-dimethylamino-3'-chloro)phenyl] 2-chloro-5-acetylamino benzoquinoneimine | 195 | $C_{16}H_{15}N_3O_2Cl_2$ | 54.54 54.46 | 4.30 4.42 | 11.93 11.64 | | |
| 12 | N-[(4'-dimethylamino-2',6'-dimethyl)phenyl] 2,6-dimethyl-3-ureido benzoquinoneimine | 240 decomposition | $C_{19}H_{24}N_4O_2$ | 67.03 66.92 | 7.11 7.00 | 16.46 16.68 | | |
| 13 | N-[(4'-dimethylamino-3'-methyl)phenyl] 2-methyl-5-carbamylmethylamino benzoquinoneimine | 214 | $C_{18}H_{22}N_4O_2$ | 66.23 66.13 | 6.79 6.65 | 17.17 17.44 | | |
| 14 | N-[(4'-dimethylamino-2'-chloro)phenyl] 6-methyl-3-(β-hydroxyethylamino benzoquinoneimine | 176 | $C_{17}H_{20}N_3O_2Cl$ | 61.17 60.94 | 5.99 6.10 | 12.60 12.51 | 10.65 10.60 | |
| 15 | N-[(4'-dimethylamino-3'-chloro)phenyl] 6-methyl-3-carbethoxy amino benzoquinoneimine | 142 | $C_{18}H_{20}N_3O_3Cl$ | 59.75 59.81 | 5.54 5.69 | 11.62 11.55 | 9.82 9.89 | |
| 16 | N-[(4'-dimethylamino-3'-chloro)phenyl] 6-methyl-3-acetylamino benzoquinoneimine, semi-hydrate | 156 | $C_{17}H_{18}N_3O_2Cl \cdot 0.5 H_2O$ | 59.91 59.87 | 5.62 5.60 | 12.33 12.38 | 10.40 10.52 | |
| 17 | N-[(4'-dimethylamino-3'-chloro)phenyl] 2,6-dimethyl-3-acetylamino benzoquinoneimine | 136 | $C_{18}H_{20}N_3O_2Cl$ | 62.52 62.54 | 5.82 5.95 | 12.15 12.24 | 10.25 10.42 | |
| 18 | N-[(4'-(dimethylamino)2,6'-dimethyl)phenyl] phenyl] 2,6-dimethyl-3-acetylamino benzoquinoneimine | 194 | $C_{20}H_{25}N_3O_2$ | 70.77 70.86 | 7.43 7.26 | 12.38 12.22 | | |
| 19 | N-[(4'-dimethyl amino)2',6'-dimethyl)phenyl] 2-methyl-5-amino benzoquinoneimine | 226 | $C_{17}H_{21}N_3O$ | 72.05 72.18 | 7.47 7.46 | 14.83 14.96 | | |
| 20 | N-[(4'-dimethylamino-2'-methyl)phenyl] 2-methyl-5-carbamylmethylamino benzoquinoneimine semihydrate | 218 | $C_{18}H_{22}N_4O_2 \cdot 0.5 H_2O$ | 64.47 64.47 64.62 | 6.86 6.86 6.91 | 16.71 16.71 16.76 | | |
| 21 | N-[(4'-dimethylamino-3'-chloro)phenyl] 2,6-dimethyl benzoquinoneimine | 62 | $C_{16}H_{17}N_2OCl$ | 66.19 66.39 | 5.58 5.73 | 9.70 9.87 | 12.27 12.47 | |
| 22 | N-[(4'-dimethylamino-2',6'-dimethyl)phenyl] 2,6-dimethyl benzoquinoneimine | 152 | $C_{18}H_{22}N_2O_2$ | 76.56 76.45 | 7.85 7.72 | 9.92 10.01 | | |

$^{(a)}$molecular weight calculated
$^{(b)}$molecular weight found by potentiometric titration in acetic acid with a 0.1 N solution of perchloric acid.

TABLE II

| Ex. No (1) | SUBSTITUTED ANILINE (11) | SUBSTITUTED PHENOL (12) | Ratio of (12):(11) (13) | Reaction Medium (14) | Oxidizing Agent (15) | Ratio of (15):(12) (16) | Temp. (°C.) (17) |
|---|---|---|---|---|---|---|---|
| 1 | N,N-dimethyl paraphenylene diamine dihydrochloride | 2-methyl-5-amino phenol | 1:1 | acetone-water 1:2 | ammonium persulfate | 1:1 | 5 |
| 2 | N,N-dimethyl paraphenylenediamine dihydrochloride | 2,6-dimethyl-3-amino | 1:1 | acetone-water 1:2 | ammonium persulfate | 1.1:1 | 0 |
| 3 | N,N-dimethyl paraphenylenediamine dihydrochloride | 2-methyl-5-ureido phenol | 1:1 | isopropanol-water 1:2 | ammonium pursulfate | 2:1 | 0 |
| 4 | N,N-dimethyl paraphenylenediamine dihydrochloride | 2,6-dimethyl-3-acetylamino phenol | 1:1 | acetone-water 1:2 | ammonium persulfate | 2:1 | 10 |
| 5 | 4-nitroso N,N-dibutylaniline hydrochloride | 2-methyl-5-carbamyl-methylamino phenol | 1:1 | ethanol-water 1:1 | | | 40 |
| 6 | 2-methyl-4-N,N-diethylamino aniline hydrochloride | 3-chloro-6-ureido phenol | 1:1 | isopropanol-water 1:1 | ammonium persulfate | 1:1 | 0 |
| 7 | 3-chloro-4-nitroso diethylaniline | 2,6-dimethyl-3-amino phenol hydrochloride | 1.1:1 | ethanol-water 1:1 | | | 35 |
| 8 | N,N-dimethyl-paraphenylene diamine dihydrochloride | 2,5-dimethyl phenol | 1:1 | acetone-water 1:1 | ammonium persulfate | 2:1 | 0-5 |
| 9 | 3-methoxy-4-nitroso N,N-dimethylaniline | 2,6-dimethyl-5-amino phenol hydrochloride | 1.1:1 | ethanol-water 1:2.5 | | | 50 |
| 10 | N,N-dimethyl paraphenylenediamine dihydrochloride | 2-methoxy-5-acetyl-amino phenol | 1:1 | acetone-water 1:3 | ammonium persulfate | 2:1 | 0 |
| 11 | 2-chloro-4-amino N,N-dimethylaniline | 2-chloro-5-acetylamine phenol | 1:1 | water | ammonium persulfate | 2:1 | 10 |
| 12 | 3,5-dimethyl-4-amino N,N-dimethylaniline dihydrochloride | 2,6-dimethyl-3-ureido phenol | 1:1 | acetone-water 1:1 | ammonium persulfate | 2:1 | 10 |
| 13 | 2-methyl-4-amino N,N-dimethylaniline | 2-methyl-5-carbamyl-methylamino phenol | 1:1 | acetone-water 1:2 | ammonium persulfate | 2:1 | 0 |
| 14 | 3-chloro-4-amino N,N-dimethylaniline | 2-methyl-5-(N-β-hy- | 1:1 | acetone-water | ammonium | 1:1 | 5 |

TABLE II-continued

| Ex. No (1) | SUBSTITUTED ANILINE (11) | SUBSTITUTED PHENOL (12) | Ratio of (12):(11) (13) | Reaction Medium (14) | Oxidizing Agent (15) | Ratio of (15):(12) (16) | Temp. (°C.) (17) |
|---|---|---|---|---|---|---|---|
| | dihydrochloride | droxyethylamino) phenol | | | 1:2 persulfate | | |
| 15 | 2-chloro-4-amino N,N-dimethylaniline | 2-methyl-5-carbethoxy phenol | 1:1 | ethanol-water 2:1 | ammonium persulfate | 2:1 | 0 |
| 16 | 2-chloro-4-amino N,N-dimethylaniline | 2-methyl-5-acetylamino phenol | 1:1 | acetone-water 1:1 | ammonium persulfate | 2:1 | 0 |
| 17 | 2-chloro-4-amino N,N-dimethylaniline | 2,6-dimethyl-5-acetylamino phenol | 1:1 | acetone-water 1:1 | ammonium persulfate | 2:1 | 5 |
| 18 | 3,5-dimethyl-4-amino N,N-dimethylaniline dihydrochloride | 2,6-dimethyl-3-acetylamino phenol | 1:1 | acetone-water 1:1 | ammonium persulfate | 2:1 | 10 |
| 19 | 3,5-dimethyl-4-amino N,N-dimethylaniline dihydrochloride | 2-methyl-5-amino phenol | 1:1 | acetone-water 1:1 | ammonium persulfate | 2:1 | 10 |
| 20 | 3-methyl-4-amino N,N-dimethylaniline dihydrochloride | 2-methyl-5-carbamylmethylamino phenol | 1:1 | acetone-water 1:2 | ammonium persulfate | 2:1 | 0 |
| 21 | 2-chloro-4-amino N,N-dimethyl aniline | 2,6-dimethyl phenol | 1:1 | 1:1 | ammonium persulfate | 2:1 | 0 |
| 22 | 3,5-dimethyl-4-amino N,N-dimethylaniline dihydrochloride | 2,6-dimethyl phenol | 1:1 | 1:1 | ammonium persulfate | 2:1 | 10 |

TABLE III

| (31) Ex. No | (32) DYE Ex. No | (33) % | (34) ADJUVANT Nature | (35) % | (36) SOLVENT Nature | (37) % | (38) Oxidizing Agent Nature | (39) ml | (40) conc. | (41) pH | (42) Hair | (43) COLOR |
|---|---|---|---|---|---|---|---|---|---|---|---|---|
| A 1 | 7 | 0.2 | | | Isopropanol | 40 | PU[1] | 100 | 10% | 9.7 | D (1 bis) | tamaris pink |
| A 2 | 2 C1[2] C2[3] | 0.15 0.15 0.10 | AL 10.5 OE[4] | 20 | | | $H_2O_2$ | 40 | 6% | 9.5 | D | pearly pink grey-beige |
| A 3 | 3 | 1.00 | LSS 19[5] EDTA[6] | 20 0.2 | | | | | | 10.7 | D | silvery blue gray |
| A 4 | 2 C3[6a] C4[7] C5[8] C6[9] | 0.40 0.40 0.20 0.40 0.10 | CMC[10] | 5 | | | $H_2O_2$ | 40 | 6% | 5.6 | B95[11] | deep gray with bronze glints |
| A 5 | 2 | 1.37 | CMC[10] | 10 | | | $H_2O_2$ | 55 | 6% | 8.5 | D | violet |
| A 6 | C7[12] | 2.05 | | | Ethanol | 50 | | | | 8.75 | B 95 | petroleum blue |
| A 7 | 1 | 0.9 | | | Ethanol | 40 | $H_2O_2$ | 100 | 6% | 9.3 | B 95 | turtle-dove gray |
| A 8 | 4 | 0.54 | AL 10.5 OE[4] | 5 | Butylglycol | 5 | | | | 10 | B 95 | metallic gray |
| A 9 | C8[13] | 3.0 | LSS 19[5] EDTA[6] 40% sodium bisulfite solution | 20 0.2 1 | | | | | | 11.3 | B 95 | eucalyptus green |
| A 10 | 6 C9[14] | 0.2 0.4 | AL 10.5 OE[4] | 5 | Butylglycol | 5 | $H_2O_2$ | 50 | 6% | 11 | B 95 | pink beige with golden glints |
| A 11 | 5 C10[15] | 0.25 2.5 | D.C.[16] | 10 | | | $H_2O_2$ | 50 | 6% | 12 | B 95 | golden honey |
| A 12 | C11[17] C10[15] | 0.25 2.5 | D.C.[16] | 10 | | | $H_2O_2$ | 50 | 6% | 12 | B 95 | light bronze |
| A 13 | C11[17] | 0.40 | D.C.[16] | 10 | | | $H_2O_2$ | 50 | 6% | 5.5 | D | Prussian blue |
| A 14 | 6 | 0.50 | MM/SM/DM[18] | 2.5 | Ethanol | 30 | | | | 7.5 | D | turquoise blue |
| A 15 | C7[12] C12[19] C13[20] C14[21] | 0.50 0.30 0.20 0.05 | VP/VA 30/70[22] | 2 | Ethanol | 40 | | | | 10 | D | very dark gray with violet glints |
| A 16 | 3 | 0.75 | VA/CA[23] M.W. = 50,000 | 1 | Ethanol | 20 | | | | 8.1 | D | blue gray |
| A 17 | 5 | 0.33 | VA/CA[23] M.W. = 10,000 | 2 | Ethanol | 50 | | | | 10.5 | B95 | silvery gray with mauve glints |
| A 18 | 2 | 0.02 | VP/VA 70/30[24] | 3 | Ethanol | 25 | | | | 8.6 | D | pearly mauve pink |
| A 19 | 21 | 0.6 | VP/VA 70/30[24] | 3 | Ethanol | 25 | | | | 9 | D | wild rose pink |
| A 20 | 9 | 0.25 | VP/VA 60/40[25] | 2 | Isopropanol | 35 | | | | 8 | D | very luminous mauve |
| A 21 | 18 | 0.25 | VP/VA 30/70[22] | 2 | Ethanol | 40 | | | | 7.5 | D | pearly pale blue |
| A 22 | 22 | 0.3 | VA/CA[23] M.W. = 70,000 | 1 | Ethanol | 36 | | | | 4.5 | D | silvery light gray |
| A 23 | 19 | 0.75 | "Gafquat 734"[26] | 2 | Isopropanol | 20 | | | | 10 | D | golden beige |
| A 24 | 12 | 0.25 | MA/MVE[27] | 1 | Ethanol | 45 | | | | 8.5 | D | pearly very light green |
| A 25 | 10 | 0.5 | PVP[28] | 2 | Isopropanol | 35 | | | | 7 | D | silvery light blue |
| A 26 | 14 | 0.5 | VA/AS/AA[29] | 2.5 | Ethanol | 50 | | | | 10 | D | deep parme |
| A 27 | 8 | 0.25 | VA/AS/AA[29] | 2.5 | Ethanol | 50 | | | | 7.5 | D | luminous silvery violet |
| A 28 | 11 | 0.35 | " | 2.5 | Ethanol | 50 | PA[30] | 5 | 2% | 10 | D | pink |
| A 29 | 13 | 0.55 | | | EMDE[31] | 8 | $H_2O_2$[32] | 40 | 6% | 11 | B 95 | pink golden beige |
| A 30 | 16 | 2 | CMC[10] | 5 | Ethanol | 20 | | | | 11 | D | pale pink with golden |

TABLE III-continued

| (31) | (32) | (33) | (34) | (35) | (36) | (37) | (38) | (39) | (40) | (41) | (42) | (43) |
|---|---|---|---|---|---|---|---|---|---|---|---|---|
| | DYE | | ADJUVANT | | SOLVENT | | Oxidizing Agent | | | | | |
| Ex. No | Ex. No | % | Nature | % | Nature | % | Nature | ml | conc. | pH | Hair | COLOR |
| A 31 | 15 | 1 | D C[16] | 8 | Ethanol | 20 | $H_2O_2$ | 25 | 6% | 10.5 | D | glints slightly mauve pink |
| A 32 | 17 | 0.75 | LSA[33] | 5 | | | $H_2O_2$ | 50 | 6% | 10 | D | slightly pink light blond |
| A 33 | 20 | 0.75 | LSS 19 | 20 | | | | | | 10.3 | D | silvery lavander blue |

[1] PU = urea peroxide (1bis)$_D$ = bleached hair
[2] C1 = 2-methoxy-4-hydroxy-4'-N,N-dimethylamino diphenylamine
[3] C2 = nitroparaphenylenediamine
[4] AL 10.5 OE = Lauryl alcohol oxyethylenated with 10.5 moles of ethyleneoxide
[5] LSS 19 = mixture of 19% of lauryl alcohol oxyethylenated with 2 moles of ethyleneoxide and 81% of the sodium sulfate salt of this same oxyethlenated alcohol
[6] EDTA = ethylene diamine tetra-acetic acid
[6a] $C_3$ = 2,4-diamino anisole dihydrochloride
[7] $C_4$ = methoxy p-phenylenediamine dihydrochloride
[8] $C_5$ = paraaminophenol
[9] $C_6$ = nitro-orthophenylenediamine
[10] CMC = Carboxymethylcellulose
[11] B 95 = 95% naturally white hair
[12] $C_7$ = 3,5-dimethyl-4-hydroxy-4'-N,N-dimethylamino diphenylamine
[13] $C_8$ = 2-acetylamino-4-hydroxy-4'-N,N-dimethylamino diphenylamine
[14] $C_9$ = 3-methoxy-4,6-diamino-4'-hydroxy diphenylamine dihydrochloride
[15] $C_{10}$ = 2-amino-4-methoxy phenol
[16] DC = diethanolamides of fatty acids of coprah
[17] $C_{11}$ = 2-methoxy-4-hydroxy-4'-N,N-dimethylamino diphenylamine
[18] MM/SM/DM = Terpolymer of methyl methacrylate (15–25%), stearyl methacrylate (25–35%) and dimethylaminoethyl methacrylate (52–62%) quaternized by dimethyl sulfate
[19] $C_{12}$ = N-[4'-(hydroxy) phenyl] 2,6-dimethyl benzoquinoneimine
[20] $C_{13}$ = 1-N-methylamino-4-N'-γ-aminopropylamino anthraquinone
[21] $C_{14}$ = nitrometaphenylenediamine
[22] VP/AV 30/70 = Copolymer of vinylpyrrolidone/vinyl acetate 30/70, M.W. = 160,000
[23] VA/CA = copolymer of vinyl acetate/crotonic/acid 90/10
70/30 =
[24] VP/VA/copolymer of vinylpyrrolidone/vinyl acetate, 70/30 M.W. = 40,000
[25] VP/VA 60/40 = Copolymer of vinylpyrrolidone/vinyl acetate, 60/40 having a viscosity of 3.3 to 4 cps at 25° C. in a 5% ethanol solution
[26] Quaternary copolymer of polyvinylpyrrolidone having a molecular weight of about 100,000, sold under the mark "Gafquat 734"
[27] MA/MVE = Monobutyl ester of the copolymer of maleic anhydride methylvinylether, 1:1, having a specific viscosity of 0.1 to 3.5 measured at 25° C. at a concentration of 1% in methylethylketone
[28] PVP = Polyvinylpyrrolidone M.W. = 40,000
[29] VA/AS/AA = Terpolymer of vinyl acetate/allyl stearate/allyloxyacetic/acid, 80.5:15:4.5
[30] PA = ammonium persulfate
[31] EMDE = monomethyl ester of diethylene glycol
[32] $H_2O_2$ = hydrogen peroxide
[33] LSA = ammonium lauryl sulfate

What is claimed is:
1. 3,2',6'-trimethyl-4-hydroxy-6-amino-4'-N,N-dimethylamino diphenylamine.
2. 3-methyl-4-hydroxy-6-amino-4'-dimethylamino diphenylamine.
3. 3,5-dimethyl-2-amino-4-hydroxy-4'-dimethylamino diphenylamine.
4. 3,5-dimethyl-4-hydroxy-2-acetylamino-4'-dimethylamino diphenylamine.

* * * * *